United States Patent [19]

Niskin

[11] Patent Number: 4,744,256
[45] Date of Patent: May 17, 1988

[54] AIRBORNE WATER SAMPLER DEVICE

[76] Inventor: Shale J. Niskin, 3415 Chase Ave., Miami Beach, Fla. 33169

[21] Appl. No.: 17,826

[22] Filed: Feb. 24, 1987

[51] Int. Cl.[4] ............................................. G01N 1/12
[52] U.S. Cl. ................................................. 73/864.66
[58] Field of Search ........... 73/864.63, 864.64, 864.65, 73/864.66, 864.67, 864.51, 864.91

[56] References Cited

U.S. PATENT DOCUMENTS

| 3,462,995 | 8/1969 | Weiss | 73/863.21 |
| 3,977,479 | 8/1976 | Sainsbury | 73/864.44 |
| 4,004,463 | 1/1977 | Puthoff et al. | 73/864.66 |
| 4,037,477 | 7/1977 | Nisken | 73/864.67 |
| 4,593,570 | 6/1986 | Niskin | 73/864.67 |
| 4,625,574 | 12/1986 | Robbins | 73/864.63 |

FOREIGN PATENT DOCUMENTS

| 958916 | 5/1964 | United Kingdom | 73/864.66 |
| 0562747 | 6/1977 | U.S.S.R. | 73/864.66 |

Primary Examiner—Stewart J. Levy
Assistant Examiner—Robert R. Raevis
Attorney, Agent, or Firm—William A. Newton

[57] ABSTRACT

Disclosed is a water sampler and method for dropping the water sampler from an airplane to obtain a sample of water from a body of water; the water sampler comprising a tubular member with ball valves at both ends and an open ended canister disposed between the ball valves, a line connected between the airplane and the tubular member for yanking the tubular member through and from the water, the yank of the line being used to move the ball valves from an initially open position to a subsequently closed position, the canister thereafter being capped and removed.

16 Claims, 5 Drawing Sheets

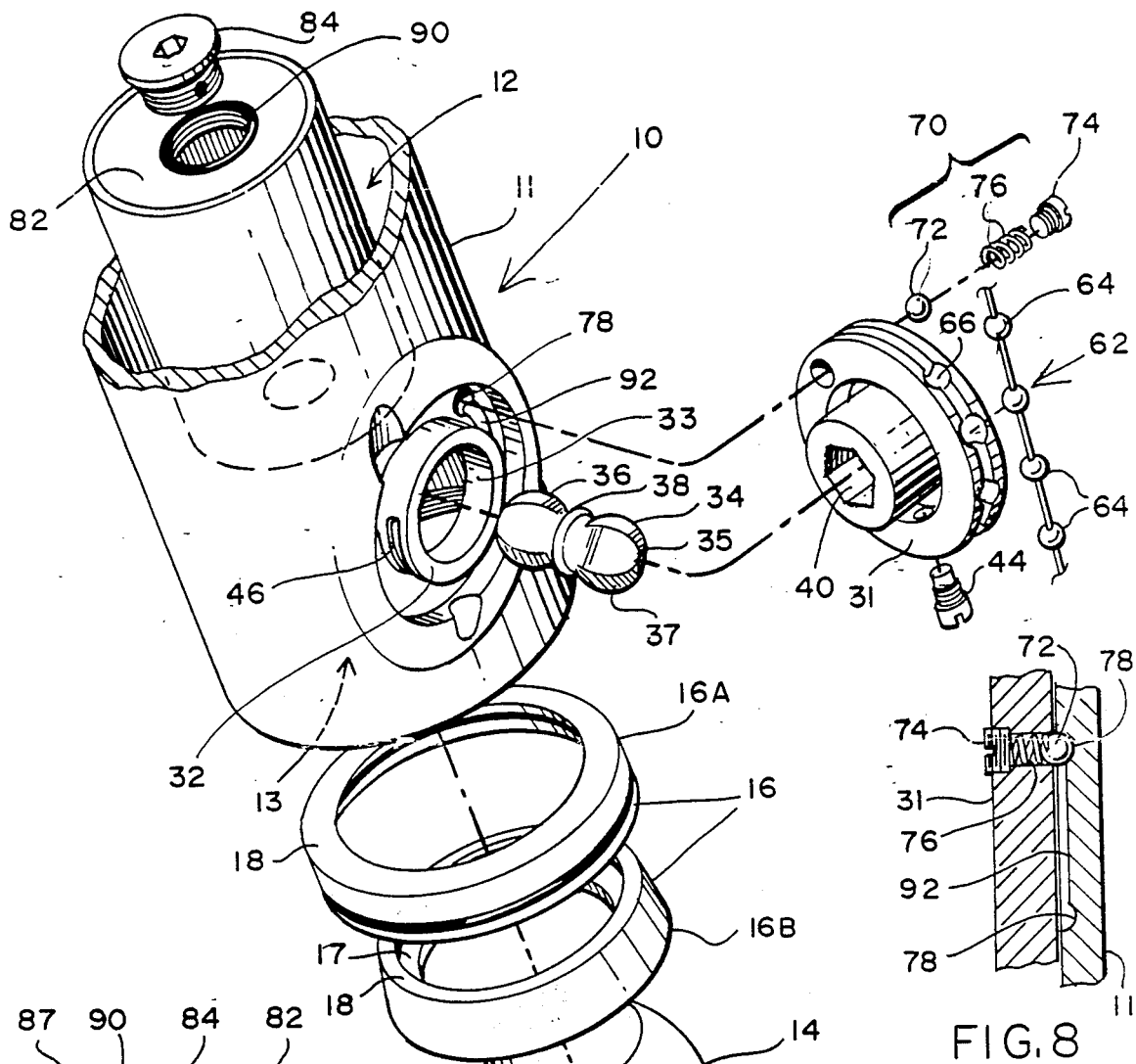
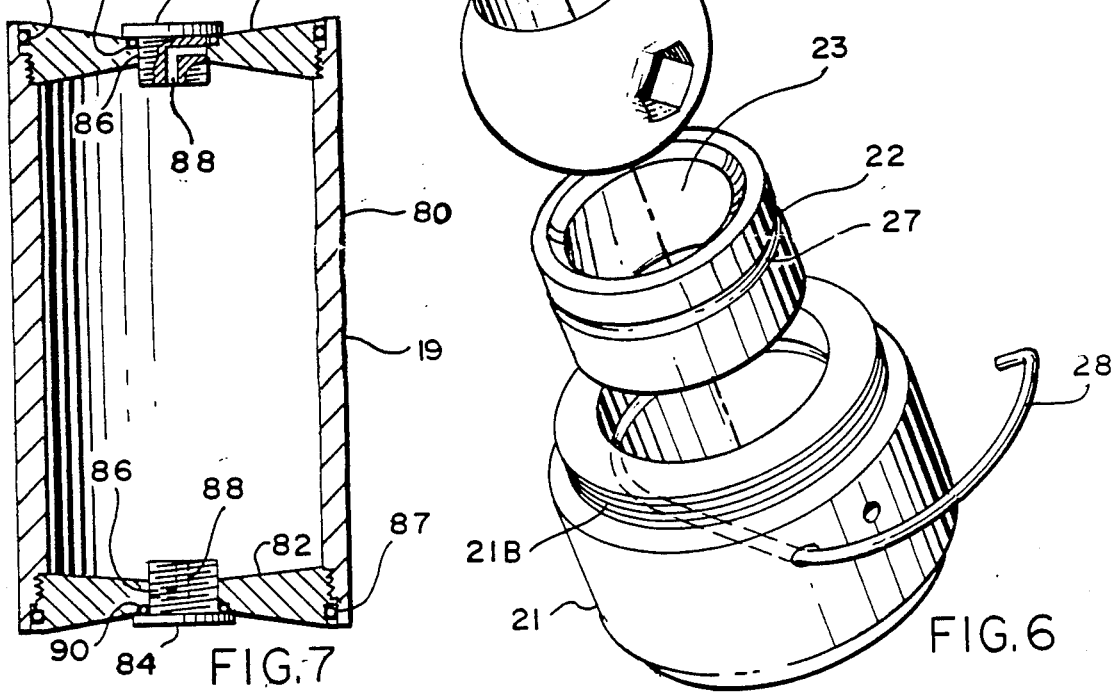

4,744,256

AIRBORNE WATER SAMPLER DEVICE

BACKGROUND OF THE INVENTION

1. Field of the Invention

This invention relates to water sample collecting devices.

2. Description of the Prior Art

The present invention is directed toward a modified version of a water sampler device shown in U.S. Pat. No. 4,593,570, which allows the same to be dropped in the air, for example, from an airplane to obtain a water sample from a body of water.

The prior art, water sampler device used for the above described purpose comprised a bucket which is dropped from a plane and which is attached to a plane by a rope. After the sampler is submerged into the water, a flapper valve seals off the sample. However, this prior art arrangement has the drawback of requiring a sampler with a 10 liter capacity in order to obtain a 5 liter sample, because approximately 50% of the sample is spilled and lost.

U.S. Pat. Nos. 4,593,570 and 3,986,635 are incorporated by reference thereto.

SUMMARY OF THE INVENTION

The present invention is implemented in a water sample collecting device having a tubular member with open end tube portions; valve means mounted at the tube end portions; the valve means comprising an outer valve seat having a substantially centrally disposed opening; an inner valve seat having a substantially centrally disposed opening, and a ball valve seated between the valve seats and having a substantially centrally disposed opening; pulley means capable of rotation by a predetermined angular amount, coupling means for coupling the pulley means to the ball valve so that rotation of the pulley means rotates the ball valve so that the openings of the valve seats and the ball valve are aligned to collect the water sample (open position) and subsequently non-aligned to contain the water sample (closed position).

The improvement of the present invention comprises dropping the tubular member into a body of water from a moving airborne object, such as an airplane, with the tubular member being attached to the moving object by a first line means so that after the momentum of the tubular member causes it to submerge into the water, the first line means yanks the tubular member through and from the body of water. A second line means, which is slack until the yank, is attached at one end to the first line means and at the other end to the pulley means by a plurality of gear balls. The yank causes the second line means to be pulled by a predetermined amount so as to rotate the pulleys through an arc of 90 degrees and thereby rotate the ball valves from the initially open position for receiving the water sample to a subsequent closed position for containing the water sample.

Prior to being dropped into the water, an open ended canister is placed in water-tight relationship between the two inner valve seats. After the water sample is obtained, most of the valve means is removed from one end and an air vented lid is attached to an exposed open end of the canister. The valve means is replaced, the canister is turned upside down and the above procedure is repeated. Thereafter, the canister, which is disposable, is removed.

BRIEF DESCRIPTION OF THE DRAWINGS

Further objects and advantages of the present invention will become apparent as the following description proceeds, taken in conjunction with the accompanying drawings in which:

FIG. 6 is an exploded view which shows the various components of the water sampler.

FIG. 7 shows the canister with both lids secured thereto so as to contain a water sample, such canister having been removed from the tubular member.

FIG. 8 shows the detent means.

DESCRIPTION OF THE PREFERRED EMBODIMENT

Figure 1A:
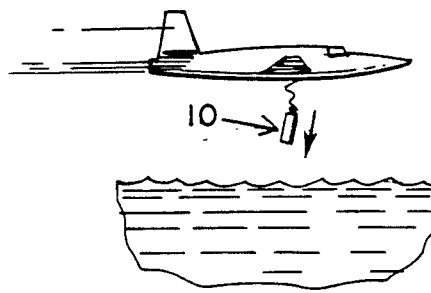
FIGS. 1A through 1D shows a water sampler of the present invention being dropped into the water and yanked out of the water by a rope attached to an airplane.
Figure 1B:
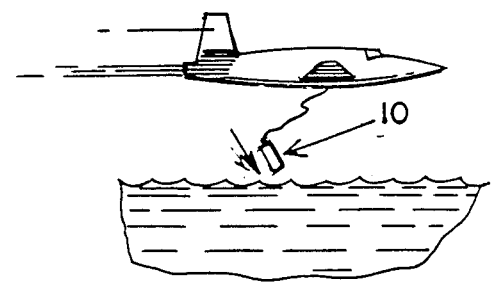
Figure 1C:
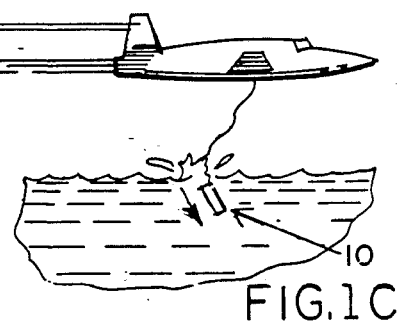
Figure 1D:
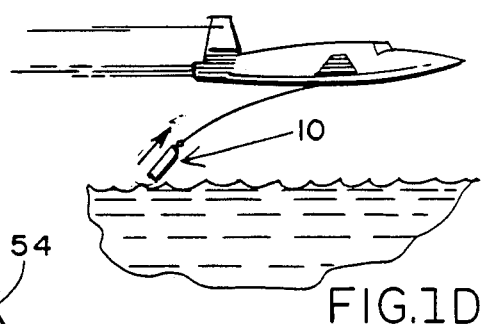
Figure 2:
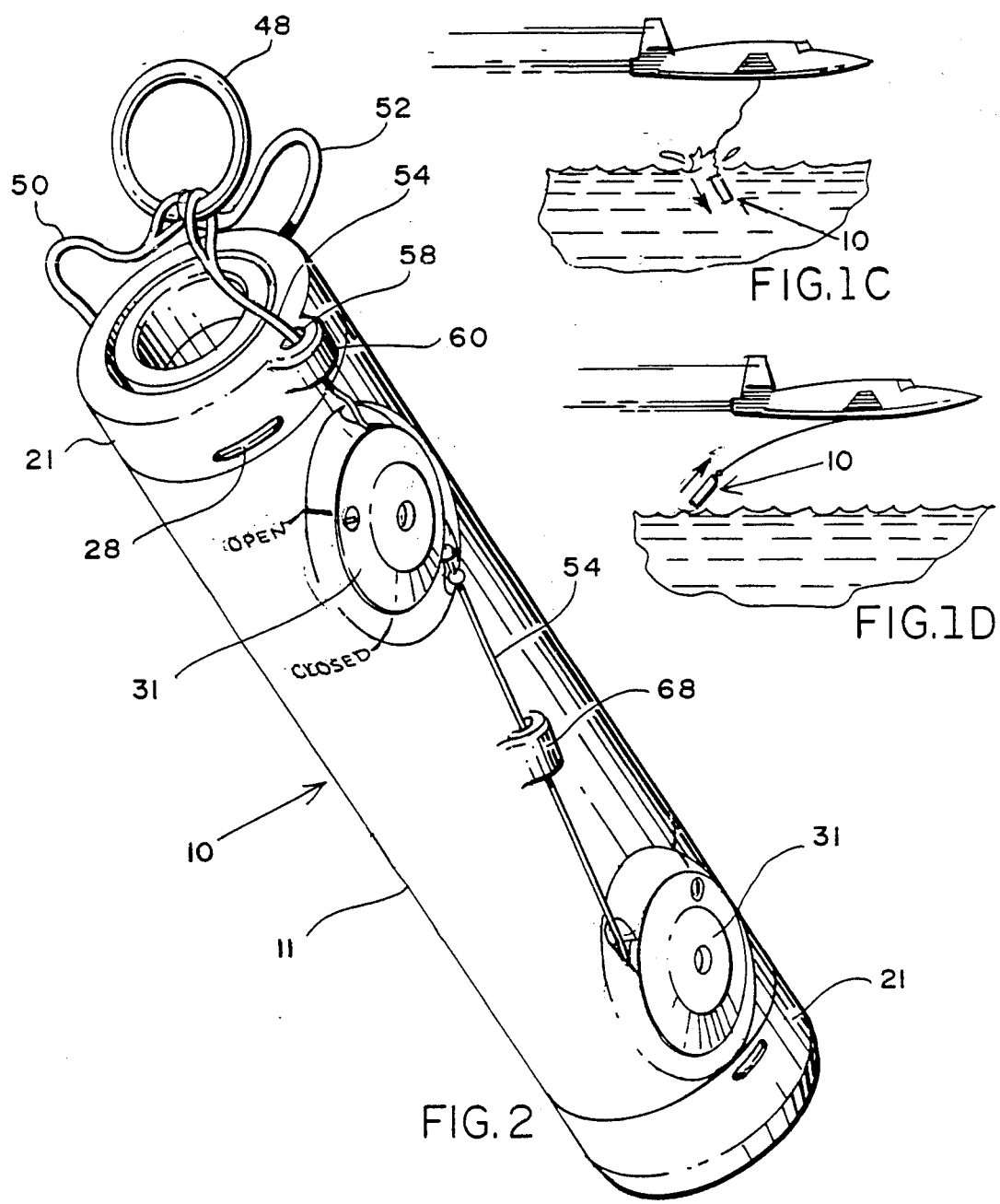
FIG. 2 is a perspective view of the water sampler.
Figure 3A:
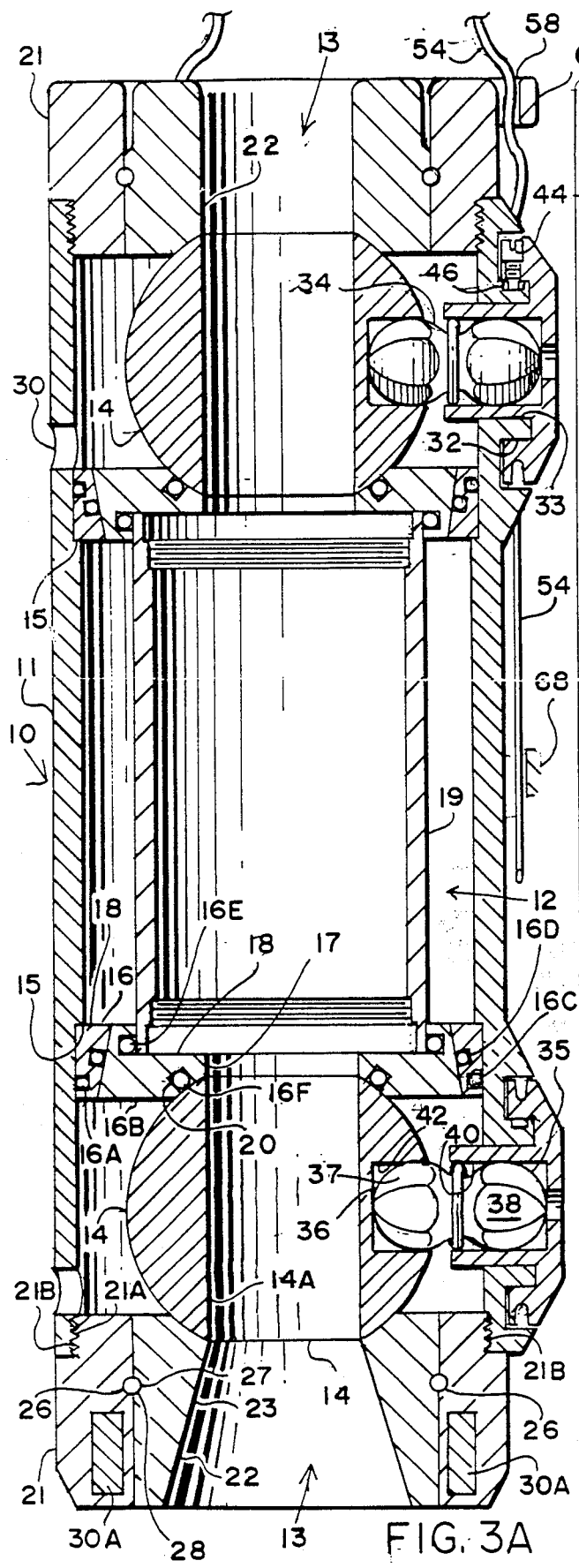
FIG. 3A is a cross-sectional view and FIG. 3B is a side view of the water sampler with its ball valves in an open position to receive the water sampler.
Figure 3B:
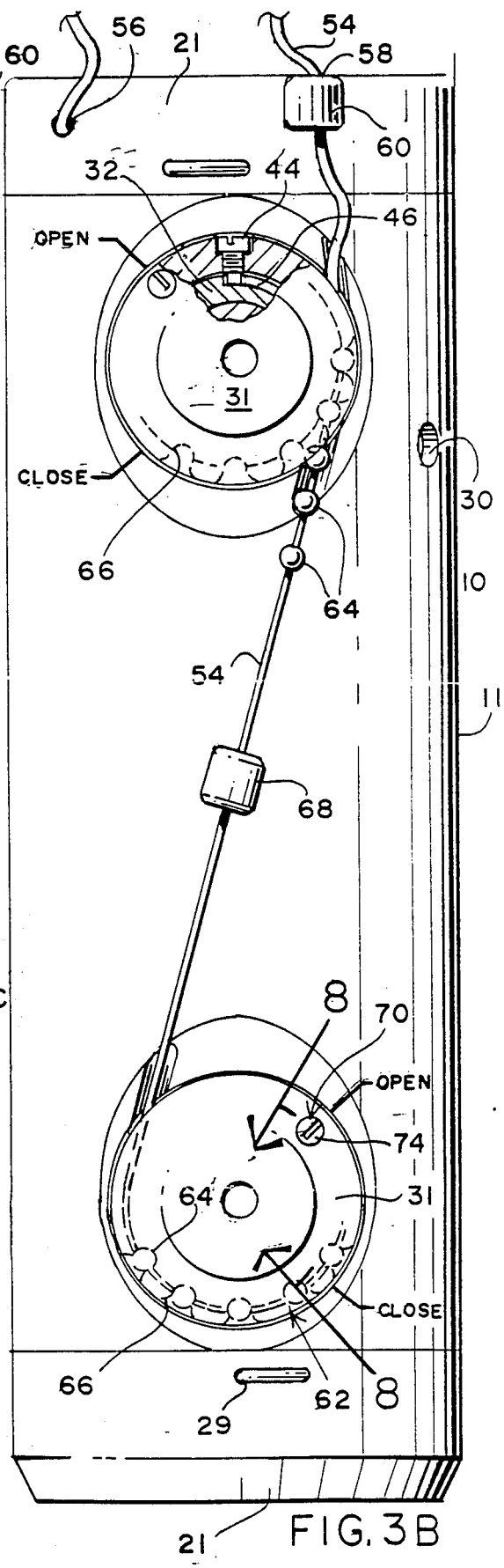
Figure 4A:
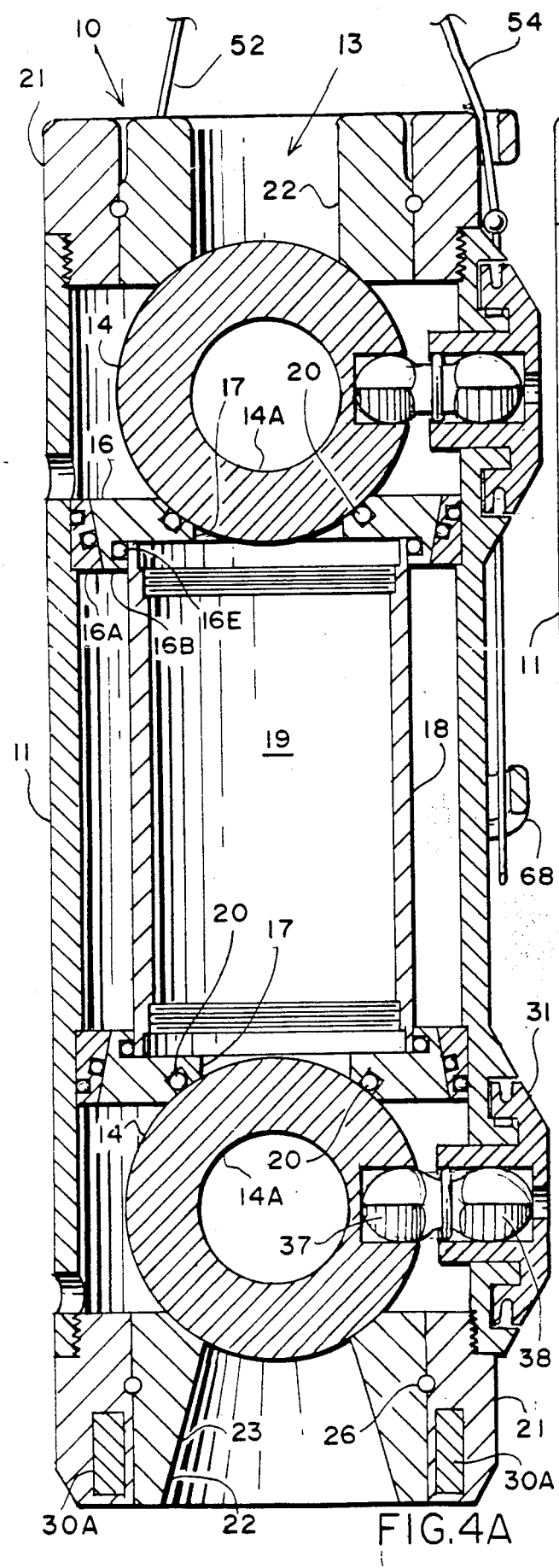
FIG. 4A is a cross-sectional view and FIG. 4B is a side view of the water sampler with its ball valves in a closed position, after the airplane has yanked the water sampler.
Figure 4B:
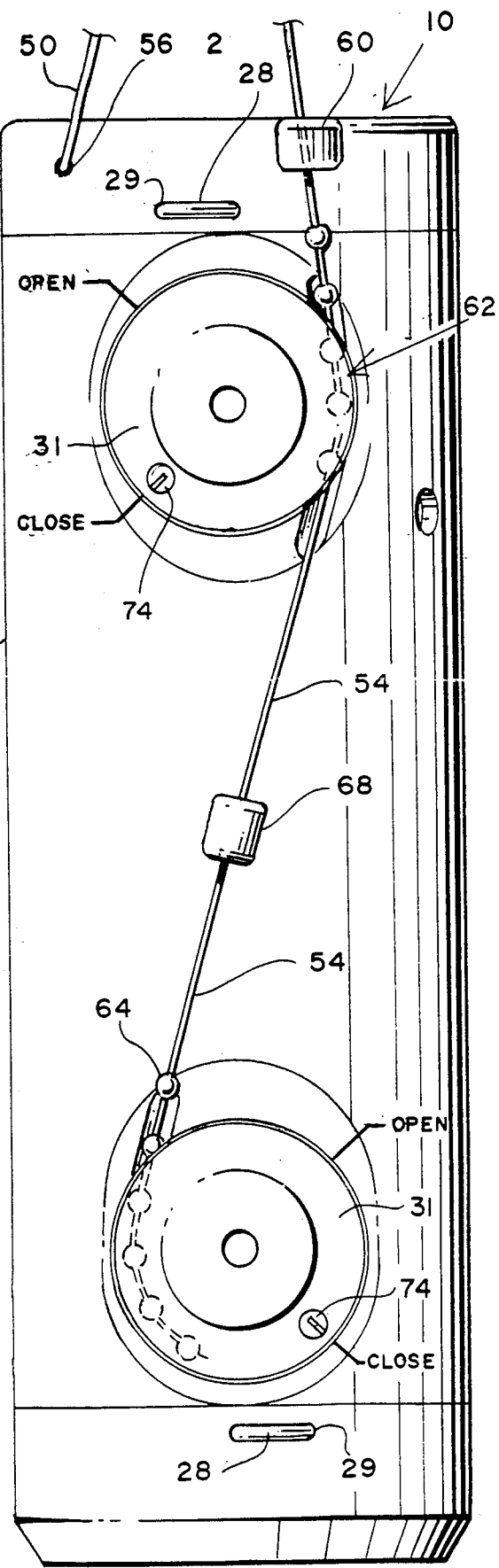
Figures 5A, 5B:
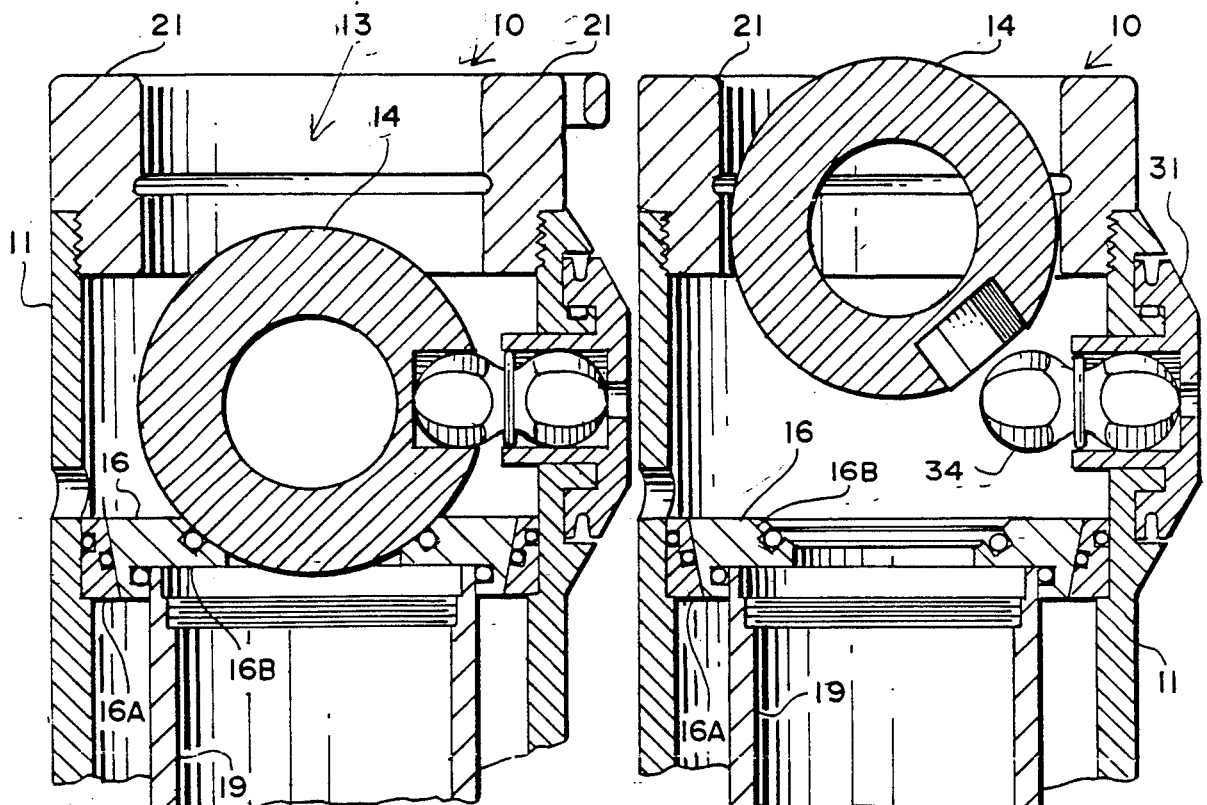
FIGS. 5A through 5D show successive steps for removing the ball valve from one end of the water sampler and placing a lid on one end of the canister prior to removing the canister from the water sampler.
Figures 5C, 5D:
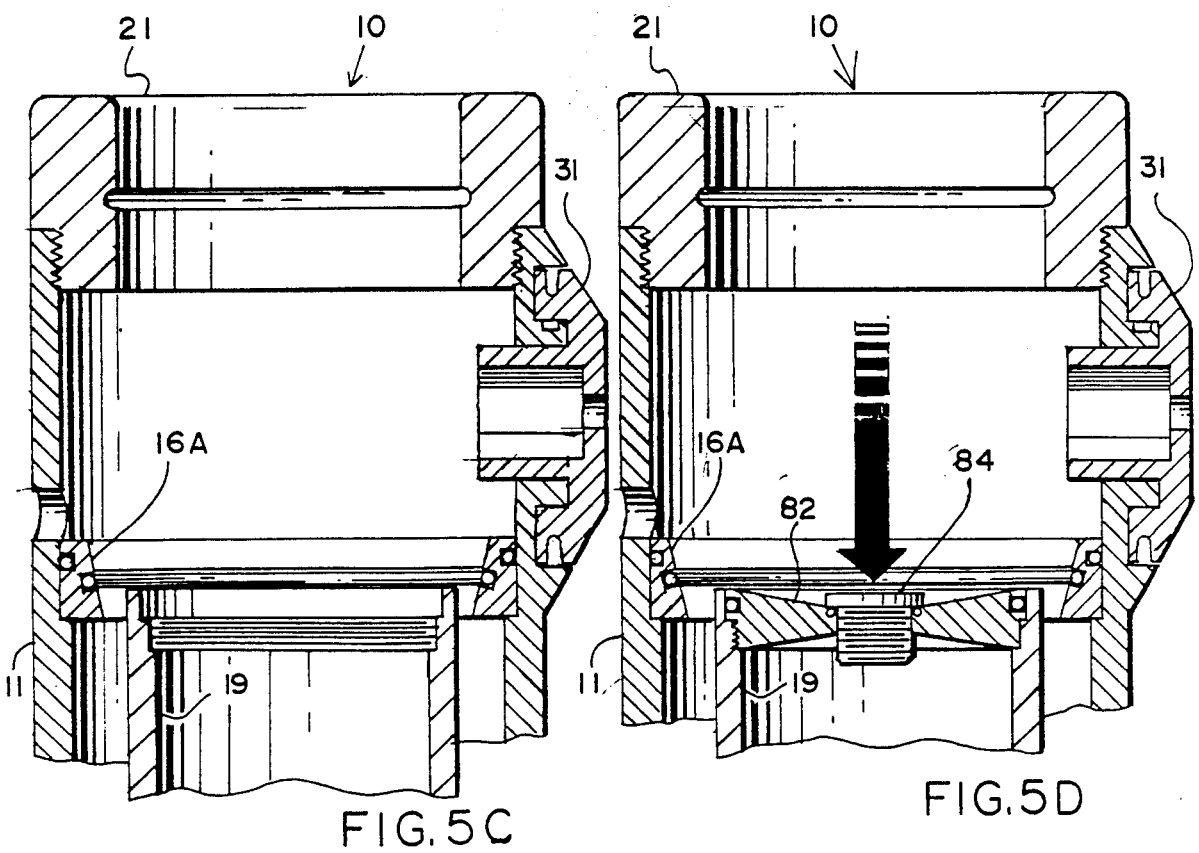

Referring to the drawings wherein like numerals are used to designate similar parts throughout the several views, the numeral 10 refers to a water sample collecting device that is a modified version of the water sampler of the incorporated U.S. Pat. No. 4,593,570 that has been adapted to be an airborne sampler that is dropped from an airplane or like airborne apparatus. As shown in Figures, the water sampler 10 consists of an elongated tubular member or bottle 11 having a chamber 12 at the ends of which are valve chambers (open end tube portions) 13. Within the valve chambers 13 are identical ball valves 14 rotatably mounted therein and having apertures 14A. Each of the valve chambers 13 is provided with a peripheral shoulder 15 on which a two part, inner ring-shaped valve seat 16 is mounted. The valve seat 16 includes a free floating, outer circular portion 16A and a free floating, inner circular portion 16B. The surfaces of portions 16A and 16B which engage each other are angled so that the inner portion 16B is wedged in a secured disposition when the ball valve 14 engages the portion 16B. O-rings 16C, 16D, 16E and 16F are disposed in grooves so as to prevent leakage of water.

The valve seat 16 that has a centrally disposed opening 17 for the flow of water therethrough is provided with outer peripheral surfaces 18 which bear on the surface 15 and on one of the ends of an interior canister 19. An inner peripheral groove 20 extending the opening 17 receives the O-ring 16F for sealing the valve seat 16 and ball valve 14 against the leakage of water therealong. The above described seat and ball arrangement is identical on both ends of the bottle.

A nose cone 21 is secured to each end of the tubular member 11 by threads 21A formed on the interior wall of the bottle which engages threads 21B formed on the nose cone 21. An outer ring-shaped valve seat 22 is mounted at the free ends of the tubular member 11 and engages the ball valves 14, thereby maintaining the ball valves 14 in a firm but rotatable condition within the chambers 13. The outer valve seats 22 are each provided with a centrally disposed opening 23. The outer valve seat 22 is secured to the tubular member 11 by peripheral matching grooves 26 and 27 formed on the inner surface of the nose cone 21 and outer surface of the outer valve seat 22 respectively and a pliable locking rod 28 (polyethylene monofil) is received therein, as shown and described in detail in incorporated U.S. Pat. No. 3,986,635. A bore 29 formed in the wall of the tubular member 11 in alignment with the grooves 26 and 27 permits the threading of a pliable rod 28 into position in the matching grooves 26 and 27 to secure the valve seat 22. As will be seen hereinafter, the nose cone 21 can be screwed on to a point which provides the desired longitudinal dimensions so that, after securing the rod 28, the seat 22 keeps the ball valve 14 and other components in position. Openings 30 formed in the side walls of the tubular member 11 provide drainage. Lead 30A in an amount of 21 lbs is inserted in the lower nose cone 21.

The ball valves 14 are actuated from an initially open position to a subsequent closed position by pulleys 31 that are each mounted on a collar 32 extending from the tubular member 11. The collar has an opening 33. As described in detail in U.S. Pat. No. 4,593,570, a key 34 has a pair of identical bulb-shaped key end portions 35 and 36, with each end portion 35 and 36 having a hexagonal cross-sectional configuration and six curved surfaces 37 and 38 respectively. Each curved surface 37 and 38 has the configuration of a wedge-shape segment or slice of a cylinder. Identical cavities 40 and 42 are formed in the pulleys 31 and the ball valves 14 for receiving the key portions 35 and 36 respectively. The cavities are dimensioned so that the key end portions can slip therein and be removed therefrom during disassembly. Likewise, the cavities 40 and 42 have a hexagonal cross-section configuration. A plurality of screws 44 extend radially through openings in the pulley 31 so as to protrude into an outer, circular groove 46 formed in the collar 32, thereby securing the pulley 31 to the collar 32.

A line, rope, from an airplane or like device is securely attached to a bridle ring 48. Preferably, but not necessarily, three polythylene impregnated, nylon ropes 50, 52, and 54 are attached at one end to the ring 48 and at the other end to the tubular member 11. More specifically, two of the ropes 50 and 52 are secured through holes 56 in one of the nose cones 21 by having a ball attached thereto. Rope 54 slidingly extends through a hole 58 formed in a protruding mount 60, which is secured to the nose cone 21, and forms part of a pair of ball gears 62, one for each of the pulleys 31. Each of the ball gears 62 comprise four balls 64 securely attached to the rope 54 in spaced apart positions that allows each of the gear balls 64 to engage and be positioned in one of the four slots 66 formed in each of the pulleys 31. As will be discussed hereinafter, when the ball valves 14 are in their closed position, the rope mount 60 acts as a stop for the outermost gear valve 64. An additional rope mount 68 preferably, but necessarily, can be used to secure rope 54.

As previously mentioned, the ball valves each have an open position wherein the center axis of aperture 14A of the ball valve 14 is substantially aligned with the center axis of the opening 23 of the seat 22 and a closed position wherein there is substantially a perpendicular relationship between the two axis. When in these two positions, each of the pulleys is secured from further rotation by a detent assembly 70. Each detent assembly includes a ball 72, a screw 74 secured in a bore formed in the pulley 31, a spring 76 positioned between the ball 72 and the screw 74 to bias the ball against two circular indentations 78 formed on the outer surface of the tubular member 11. When in either the closed or open position, the spring 76 causes the ball 72 to be secured in the indentations 78, thereby preventing any further rotation without substantial force. The biasing force can be adjusted by the screw 74.

The canister 19 is the sample container. The canister 19 includes a cylindrical body 80, a pair of opposed lids 82, and a pair of air vent screws 84 which each threadingly engages the walls of a threaded hole 86 formed in one of the lids 82. Additionally, each lid includes an O-ring 87 to form a water-tight seal. With small enough samples, only O-ring 87 is necessary. However, in the illustrative embodiment, the edges of the lids 82 includes threads that engage threads on the interior wall of the canister 19, so that the lids are screwed onto the end of the canisters. During the time when the water sample is obtained, the lids are removed. Each air vent screw includes an L-shaped tubular hole 88 and an O-ring 90.

In operation, the water sampling device 10 is dropped from an airplane, typically from a height in the range of 150 feet above a surface of a body of water. Typically, the rope attached to the bridle ring 48 plays out of a bucket. The pulleys 31 are set so that the ball valves 14 are in their open positions. At this point, the ropes 50, 52, and 54 will be relatively slack. The momentum of the device 10 causes it to submerge in the water for 2 to 5 seconds until the line goes taut. As the line goes taut, it yanks the ball valves 14 from an open position to a closed position. More specifically, the yank jerks the ball 72 out of its indentation 78 in the tubular member, allowing the pulleys 31 to rotate through an arc of 90 degrees, as the gear balls 64 engage successive slots 66. When the pulleys 31 (and therefore the ball valves 14) have rotated 90 degrees from its open position to its closed position, the uppermost gear ball 64 engages the rope mount 60 so that further pull on the rope 58 below the mount 60 is prevented. At this point, the ball 72 protrudes into a second indentation, so as to prevent any further rotation of the pulleys 31. Typically, there is 1000 lbs of pull by the water on the device 10.

After the sampler device 10 has been removed from the water, the canister 19 is removed in the manner described hereinafter. The canister 19 is disposable. First, the sample device is held in an upright, vertical position with one end of the canister being up. The pliable rod 28 is removed from the nose cone 21 at the upright end. The outer valve seat 22 is lifted out, thereby providing clearance for the removal of the upper ball valve 14. The ball valve 14 is removed, then the inner portion 16B of the inner valve seat 16 is removed. Then one of the lids 82 is screwed on the exposed upper end of the canister 19. The top air vent screws are initially in their loose position, so that air can escape from it as the lid 82 is being screwed down. When the water starts to flow out of the air vent screw, it is screwed down tight to prevent any further leakage. The inner portion 16B, ball valve 14 and outer valve seat 22 are replaced and the pliable rod 28 is put back in place. The sampler device 10 is then turned end for end and the above procedure is repeated, with the seat 22, ball valve 14, and inner portion 16B being removed and the second lid 82 being screwed on and the air being vented from the canister. At this point, with lids 82 to both ends of the canister 19, the canister is removed from the tubular member 11. As previously mentioned, for small samples, the lids do not need threads. This is because there is no access for the air into the canister and therefore a vacuum seal is provided which is enough to hold the lids on.

Typically, the sampler device 10 is neutrally buoyant, for example, with a buoyancy of 0.98. In the illustrative embodiment, the sampler device 10 weighs 53 lbs, the canister 19 weighs 4.2 lbs, with the canister having a 6 liter capacity. The tubular member 11, nose cones 21, seats 16 and 23, and canister 19 are made of H.D. polyethylene. The bridle ring 48 is made of nylon and the O-rings of polyethylene. Typically, the interior diameters of the tubular member 11 and the canister 19 are, respectively, 8.6 and 5 inches. The ball valves 14 typically have a 6 inch diameter with a 3.5 inch aperture 14A. The tubular member typically has an overall length of 37 inches.

In an alternative embodiment, it is contemplated that a rope separate from those used to elevate the device 10 can be used to rotate the pulleys. In this case, the line would include a stretch compensator and none of the gear balls would engage the rope mount.

Preferably, a semicircular groove 92 connects the two indentations and has a curved cross-section. The depth of the groove 92 into the tubular member 11 is less than the indentations and allows for the ball 72 and therefore the pulley 31 to move from their open position to their closed position. However, the lack of a groove elsewhere presents rotation except between the two indentations.

Although particular embodiments of the invention have been shown and described here, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. In a water sampler collecting device for collecting a water sample having a tubular member with a pair of open end tube portions; a pair of valve means mounted at said open end tube portions; each of said valve means comprising an outer valve seat having a substantially centrally disposed opening, an inner valve seat having a substantially centrally disposed opening, and a ball valve seated between said valve seats and having a substantially centrally disposed opening; a pair of pulley means capable of rotation by predetermined angular amount, a pair of coupling means for coupling said pulley means to each said ball valve so that rotation of said pulley means rotates said ball valve whereby said openings of said valve seats and said ball valve are in aligned open disposition to collect the water sample and are in non-aligned closed disposition to contain the water sample, the improvement comprising:

first line means for pulling said tubular member;
second line means being attached to said first line means and said pulley means and being responsive to a yank on said first line means to cause said pulley means to rotate each of said ball valves from an initial said aligned open disposition to a subsequent said non-aligned closed disposition;
said first line means is for pulling said tubular member through and out of a body of water and said yank on said first line means is caused by said tubular member engaging said body of water; and
said first line means is connected at one end to an airborne vehicle and at the other end to said tubular member.

2. A method of collecting a water sample comprising:
providing a tubular member with a pair of open end tube portions, each of which contains a ball valve rotatably mounted between an inner valve seat and an outer valve seat;
setting said ball valves to an initially open position to receive said water sample;
attaching a first line between an airborne moving object and said tubular member and dropping said tubular member from said moving object into a body of water so that said tubular member submerges into said body of water and causes a yank on said first line; and
using said yank of said first line to provide the force necessary to rotate said ball valves to a closed position.

3. The method of claim 2, wherein said step of using said yank includes using said yank to rotate through an arc of approximately 90 degrees a pair of pulleys coupled to said ball valves.

4. The method according to claim 3, further including a step of mounting a removable canister inside said tubular member prior to the step of dropping said tubular member, said canister having opposed ends that are open.

5. The method according to claim 4, further including steps of removing said outer valve seat, said ball valve, and at least a portion of said inner valve seat from an upright end of said tubular member after said tubular member has been removed from said body of water; thereafter placing an air vented lid on an exposed end of said canister; and thereafter putting back into position said outer valve seat; said ball valve; and said at least a portion of said inner valve seat.

6. The method according to claim 5, further including after said step of placing said lid, a step of turning said tubular member end to end; thereafter a step of removing the other said outer valve seat, said ball valve and at least a portion of said inner valve seat from said tubular member; thereafter a step of placing another lid on the other end of said canister, and thereafter a step of removing said canister.

7. In the method according to claim 2, wherein said airborne moving object comprises an airplane.

8. In a water sampling system comprising:
vehicle means operable for airborne movement;
a water sample collecting device means for collecting a water sample when dropped from said vehicle means;
first line means being connected between said water sample collecting device means and said vehicle means for pulling said water sample collecting device through and out of a body of water;
said water sample collecting device having a tubular member with a pair of open end tube portions; a pair of valve means mounted at said open end tube portions; each said valve means comprising an outer valve seat having a substantially centrally disposed opening, an inner valve seat having a substantially centrally disposed opening, and a ball valve seated between said valve seats and having a substantially centrally disposed opening; a pair of pulley means capable of rotation by predetermined angular amount, a pair of coupling means for coupling said pulley means to each said ball valve so that rotation of said pulley means rotates said ball valve whereby said openings of said valve seats and said ball valve are in aligned open disposition to collect the water sample and are in non-aligned closed disposition to contain the water sample; and second line means being attached to said first line means and said pulley means and being responsive to a yank on said first line means to cause said pulley means to rotate each of said ball valves from an initial said aligned open disposition to a subsequent said non-aligned closed disposition.

9. In the water sampling system of claim 8, wherein said second line means includes a line and a plurality of gear balls distributed along said line connected to said first line means and disposed to engage a plurality of slots on the periphery of each of said pulley means, said second line means responsive to said yank on said first line means to cause said gear balls to engage successive slots along said pulley means so as to rotate said pulley means through an arc of approximately 90 degrees.

10. In the water sampling system of claim 9, wherein said first line means includes a first line connected to a bridle and a plurality of support lines connected from said bridle to said tubular member, said line of second line means consists of one of said support lines which is extended through a line of mount and has a disposed therealong said plurality of gear balls for rotating said pulley means and one enlargement disposed therealong for engaging said line mount to stop further rotation of said pulley means.

11. In the water sampling system of claim 8, wherein said vehicle means comprises an airplane.

12. In a water sampler collecting device for collecting a water sample having a tubular member with a pair of open end tube portions; a pair of valve means mounted at said open end tube portions; each of said valve means comprising an outer valve seat having a substantially centrally disposed opening, an inner valve seat having a substantially centrally disposed opening, and a ball valve seated between said valve seats and having a substantially centrally disposed opening; a pair of pulley means capable of rotation by predetermined angular amount, a pair of coupling means for coupling said pulley means to each said ball valve so that rotation of said pulley means rotates said ball valve whereby said openings of said valve seats and said ball valve are in aligned open disposition to collect the water sample and are in non-aligned closed disposition to contain the water sample, the improvement comprising:

first line means for pulling said tubular member;
second line means being attached to said first line means and said pulley means and being responsive to a yank on said first line means to cause said pulley means to rotate each of said ball valves from an initial said aligned open disposition to a subsequent said non-aligned closed disposition;
a removable canister for containing the water sample mounted in said tubular member between said pair of valve means, said canister having opposed ends open when in a body of water; and
said canister includes a pair of lids, each of said lids including an air vent having an opened condition and closed condition.

13. In the water sample collecting device of claim 12, wherein said canister initially has its opposed open ends in water-tight engagement with said inner valve seats and without said lids attached, said valve means being removable to allow placement of said lids on the ends of said canister and for removal of said canister.

14. In the water sample collecting device of claim 12, wherein each said inner valve seat includes an outer circular portion and an inner circular portion, said tubular member including a cylindrical housing portion and at each end thereof a pair of nose cones which threadingly engages said cylindrical housing portion so as to adjust the longitudinal dimensions of said tubular member, each said outer valve seat being secured to one of said nose cones by a pliable rod disposed in a pair of opposed grooves, one of said grooves being in said nose cone and the other said groove being in said outer valve seat, said outer circular portion, said ball valve, and said outer valve seat being removable to allow for removal of said canister.

15. In a water sampler collecting device for collecting a water sample having a tubular member with a pair of open end tube portions; a pair of valve means mounted at said open end tube portions; each of said valve means comprising an outer valve seat having a substantially centrally disposed opening, an inner valve seat having a substantially centrally disposed opening, and a ball valve seated between said valve seats and having a substantially centrally disposed opening; a pair of pulley means capable of rotation by predetermined angular amount, a pair of coupling means for coupling said pulley means to each said ball valve so that rotation of said pulley means rotates said ball valve whereby said openings of said valve seats and said ball valve are in aligned open disposition to collect the water sample and are in non-aligned closed disposition to contain the water sample, the improvement comprising:

first line means for pulling said tubular member;
second line means being attached to said first line means and said pulley means and being responsive to a yank on said first line means to cause said pulley means to rotate each of said ball valves from an initial said aligned open disposition to a subsequent said non-aligned closed disposition;
said second line means includes a line and a plurality of gear balls distributed along said line connected to said first line means and disposed to engage a plurality of slots on the periphery of each of said pulley means, said second line means responsive to said yank on said first line means to cause said gear balls to engage successive slots along said pulley means so as to rotate said pulley means through an arc of approximately 90 degrees; and
said first line means includes a first line connected to a bridle and a plurality of support lines connected from said bridle to said tubular member, said line of said second line means consists of one of said support lines which is extended through a line mount and has disposed therealong said plurality of gear balls for rotating said pulley means and one enlargement disposed therealong for engaging said line mount to stop further rotation of said pulley means.

16. In the water sample collecting device of claim 15, wherein said pulley means include detent means for engaging a pair of indentations on said tubular member when said ball valves are in said closed and open dispositions.

* * * * *